(12) United States Patent
Olive et al.

(10) Patent No.: US 7,568,446 B2
(45) Date of Patent: Aug. 4, 2009

(54) METHOD FOR INDUCING THE SEXUAL MATURATION OF LUGWORMS

(75) Inventors: Peter James William Olive, Tyne & Wear (GB); Stephen Craig, Northumberland (GB)

(73) Assignee: Seabait Limited, Ashington, Northumberland (GB)

( * ) Notice: Subject to any disclaimer, the term of this patent is extended or adjusted under 35 U.S.C. 154(b) by 544 days.

(21) Appl. No.: 10/577,790

(22) PCT Filed: Oct. 29, 2004

(86) PCT No.: PCT/GB2004/004596

§ 371 (c)(1),
(2), (4) Date: Jul. 18, 2006

(87) PCT Pub. No.: WO2005/043994

PCT Pub. Date: May 19, 2005

(65) Prior Publication Data

US 2007/0074666 A1    Apr. 5, 2007

(30) Foreign Application Priority Data

Oct. 30, 2003 (GB) .................................. 0325304.4

(51) Int. Cl.
*A01K 29/00* (2006.01)
(52) U.S. Cl. ....................................................... 119/6.7
(58) Field of Classification Search .................. 119/6.7, 119/6.5, 6.6, 270
See application file for complete search history.

(56) References Cited

U.S. PATENT DOCUMENTS

| 3,961,603 | A | * | 6/1976 | Gaddie, Sr. ................... 119/6.7 |
| 4,417,545 | A | * | 11/1983 | Finney ........................ 119/6.6 |
| 4,513,685 | A | * | 4/1985 | Frijters et al. ................ 119/6.7 |
| 5,664,366 | A | * | 9/1997 | Lopuszanski et al. .......... 43/55 |
| 6,193,902 | B1 | * | 2/2001 | Eguchi ............................ 252/1 |
| 6,360,688 | B1 | * | 3/2002 | Olive ........................... 119/6.7 |

FOREIGN PATENT DOCUMENTS

WO    WO 98/06255 A    2/1998

OTHER PUBLICATIONS

Watson et al., "Control of oocyte maturation, sperm activation and spawning in two lugworm species: Arenicola marina and A. defodiens", *Marine Ecology Progress Series* 175:167-176 (Dec. 17, 1998).

* cited by examiner

*Primary Examiner*—Yvonne R. Abbott
(74) *Attorney, Agent, or Firm*—Drinker, Biddle & Reath, LLP

(57) ABSTRACT

The present invention provides a method for inducing gamete maturation in marine worms of the family arenicolidae and which exhibit epidemic spawning. In the method, male and/or female worms in a housing substrate (such as sand) in sea water are maintained at a temperature of 4 to 8° C. for 14 to 24 days, preferably 5 to 7° C. for 20 to 22 days. Spawning of the worms can them be induced either by exposure to suitable spawning promoting hormones or by raising the temperature of the sea water to 12 to 14° C.

10 Claims, No Drawings

METHOD FOR INDUCING THE SEXUAL MATURATION OF LUGWORMS

The present invention relates to the aquaculture of marine worms and particularly to the control of sexual maturation of marine worms.

Marine worms are animals in the Class Polychaeta of the Phylum Annelida or in the Phylum Sipunculida. Such worms are the natural foodstuff for fish, crustaceans and other marine organisms, and therefore find utility as bait for anglers and other fishermen. Additionally certain marine worms have been extensively studied and are recognised as being useful for toxicity testing and other scientific purposes. Marine worms also find utility as a dietary item for aquaculture either in fresh or frozen form or incorporated into food products in a variety of formulations.

However, the natural supply of marine worms is finite and serious concerns have been raised regarding the potential environmental damage caused by unsustainable over harvest. An environmentally acceptable alternative to collecting marine worms from the wild is their aquaculture to provide a sustainable supply. The aquaculture of marine worms provides the additional benefit of known and quantified content of specified biochemical content and the certifiable absence of specific pathogenic organisms providing aquaculture feeds that may be designated as having Specific Pathogen Free status.

The aquaculture of the polychaete worms Arenicolidae (commonly known as "lugworms") has attracted some interest (see Gambi et al., 1994; Olive 1993), especially since bait digging for these animals was considered to be a cause of environmental damage (see Olive, 1993).

*Arenicola marina* (lugworm) is an iteroparous polychaete, breeding several times per lifetime, but at annual intervals (Clark and Olive, 1973). *A. marina* is a marine deposit feeder (Jumars, 1993; Fauchald and Jumars, 1979) and ingests sand grains or other substrate at the head of the horizontal section of a J-shaped burrow in which the animal resides.

An attempt to culture *A. cristata* was described by D'Asaro et al., 1976 but did not lead to commercial aquaculture of any species of lugworm using the methods described. A more successful methodology for the aquaculture of deposit feeding marine worms has since been described in our published International Patent Application No. WO-A-03/007701. The methodology described relates to a method of successfully farming the worms or their larvae, such that the body weight of the worms increases. However, the methodology described in WO-A-03/007701 offers no means to control the breeding period of the worms.

D'Asaro describes a method to induce spawning in the lugworm *Arenicola cristata*, by maintaining the broodstock at temperatures of 18 to 32° C. In the wild, female *Arenicola cristata* worms will produce egg masses at frequent intervals throughout the year and D'Asaro describes using temperatures of 16-18° C. or above to stimulate the release of up to 4 egg masses a month for cultured female worms.

By contrast, the *Arenicola marina* and *Arenicola defodiens* populations spawn annually in a discrete period lasting 4 to 5 days. Simultaneous spawning of the local population of a single species in this way is termed "epidemic spawning". The spawning of discrete populations in neighbouring locations may vary by several days or even weeks, whilst the date of spawning—even at a single location—may vary by as much as 4 to 5 weeks in subsequent years. Since *Arenicola marina* exhibits epidemic spawning it has been postulated that external factors could determine, or at least influence, the date of spawning within a single population.

A study by Watson et al., 2000 examined various external factors (specifically environmental factors) and assessed their influence on the date of spawning within a Scottish population of *Arenicola marina*. The external factors reviewed were the sea and air temperatures, tidal cycle, air pressure, rainfall and windspeed/direction. The study noted that the population studied always spawned on the spring tides and suggested that spawning correlated with the tidal cycle with a semi-lunar periodicity. It was also suggested that a drop in temperature could operate as a cue to spawning, but Watson et al., 2000 concluded that their data did not indicate any threshold temperature or reduction in temperature necessary to induce spawning.

In conclusion, it is clear from the literature that the lugworms *Arenicola marina* and *Arenicola defodiens* reproduce only during a very short period of the year and that the date of spawning is not easily predictable. In terms of the aquaculture of lugworms such as *Arenicola marina* or *Arenicola defodiens* that are normally found in temperate or boreal regions, it would be of great benefit to be able to induce the spawning of the worms in order to maintain the farmed population at the levels required.

We have now found that the careful manipulation of temperature can induce spawning in both male and female marine worms of *Arenicola marina* and *Arenicola defodiens* such that reproduction can be made to occur at all times of the year and this ability to induce sexual maturation represents a significant advance in aquaculture of these worms.

The present invention thus provides a method of inducing gamete maturation to the point of competence to fertilise in marine worms of the family Arenicolidae which exhibit epidemic spawning, said method comprising:

providing maturing male worms and/or maturing female worms wherein said worms are provided in a housing substrate in sea water at a temperature of 4 to 8° C. for a time period of 14 to 24 days.

The term "epidemic spawning" as used herein is as defined in Watson et al., 2000 as the synchronized spawning of a local population of a single species. "Epidemic spawning" is thus distinguished from "mass spawning" which is used to describe the synchronised spawning of population of several species at a given locale (see Babcock et al., 1986).

In one embodiment the worms are maintained at a temperature of approximately 6° C. (eg. 5 to 7° C.) for 14 to 24 days.

In one embodiment the worms are maintained at a temperature of 4 to 8° C. (for example 5 to 7° C.) for at least 18 days and typically 20 to 22 days.

Reference is made above to the worms being held at a temperature of 4 to 8° C. (preferably 5 to 7° C.) for a period of 14 to 24 days. The exact time period will depend upon the condition of the worms for spawning as assessed by measuring the diameter of the coelomic oocytes (eggs) for female worms, or in male worms by measuring the percentage of the groups of male sperm cells (platelets) wherein the sperm tails have differentiated (morulae) in samples of coelomic fluid obtained by biopsy. The biopsy may be carried out by inserting a hypodermic needle into the tail region of the body parallel to the long axis of the body in order to avoid possible damage to the blood vessels and vital organs present in the non-tail region of the animal's body.

In one embodiment, the present invention induces spawning (i.e. gamete release) of the worms. However, we have found that the effect of temperature of 4 to 8° C. promotes the maturation of gametes so that the gametes are ready for release in spawning under appropriate hormonal control. These mature gametes could be harvested from the parent worm such that fertilisation can occur in vitro. Gamete release can be achieved by the natural release of a hormone or may, if preferred, be achieved by the injection of a homogenate of the prostomium in sterile filtered seawater at a concentration of 1 prostomium equivalent per worm (for females). In the case of male worms gamete release can be induced by injection of 8, 11, 14-eicosatrienoic acid (usually dissolved in methanol and diluted with seawater) to give a final concentration in the body cavity of approximately $1 \times 10^{-4}$ M. Similar procedures are described in the literature (Bentley et al. 1990 and Bentley et al. 1996) to induce gamete release from animals ready to spawn during the natural breeding season.

The present invention is suitable for maturing female worms and for maturing male worms of the family Arenicolidae. Maturing female worms are defined as female worms observed to possess coelomic eggs having a modal diameter of at least 160 microns. Usually the observation is made by coelomic biopsy, a technique routine in the art. Briefly, a coelomic biopsy involves removal of a sample of coelomic fluid by means of a hypodermic syringe (a 25 g hypodermic needle is suitable) and examining the sample taken by light microscope. Maturing male worms are defined as male worms observed to possess a ratio of morulae to spermatocytes of 80% or more. Usually this observation is made by examining a small sample of coelomic fluid obtained as described above on a microscope slide using a ×10 objective lens and examining approximately 100 groups of male germ cells (spermatocytes in the form of platelets or morulae as mentioned above). Maturing worms are present in samples of worms which have been cultured at a temperature of approximately 16° C. (eg 14 to 18° C.) for a period of 3 to 5 months. These maturing worms can be selected for use in the present invention. We have found that allowing the maturing worms to remain at the culture temperature (of approximately 16° C.) results in degeneration of the maturing gametes without spawning, before the worms start the maturing cycle once more.

The substrate housing the worms may be any particulate material suitable for a deposit feeding worm. Typically a sandy substrate may be used, but other particulate materials (eg. glass beads) having particles of a similar size could also be used. Sand is preferred due to its wide availability and low cost.

A suitable depth of substrate is provided to house the worms. A depth of approximately 5 cm is sufficient for the worms to form their habitual housing tubes. Whilst greater depths of substrate (for example up to 10 cm, even 20 to 40 cm) is possible, this increases the associated cost of the procedure. For ease of harvesting the worms the minimum depth of substrate is desirable.

The sea water used in the present method may be filtered seawater (eg. filtered twice through a filter having 0. 34 μm pore size), a flow through system receiving natural sea water or recirculated in an aquaculture system incorporating biofiltration, a protein skimmer and/or other water treatment devices as are readily available from commercial sources.

For the purposes of hygiene management, we have found it convenient if the substrate housing the worms contains little or no food material with no additional food material being provided during the time period of 14 to 24 days. The presence of little or no food allows the cleanliness of the water to be easily maintained to a high standard, without affecting the worms adversely since the time period in question is short.

The method described herein can be used to induce spawning in any species of worm belonging to the family Arenicolidae. Species of particular interest include *Arenicola marina* and *Arenicola defodiens*.

The method is suitable for maturing females and/or maturing males (as defined above) collected from natural populations in the wild or, more preferably, cultured according to the methodology of WO-A-03/007701. Where the worms have been cultured we have found that the best results are obtained using worms maintained (with adequate food supply) at a temperature of 16° C. for 3 to 5 months. Good results can also be obtained if the culture temperature is 14° C. or more, for a period of at least one month.

For commercial purposes, it may be desirable to allow male and female worms to spawn in isolation in small containers of sea water and to selectively mix the oocytes and spermatozoa, and to select for fertilised eggs after induced spawning by the methods described above.

We have found that if there are any unspawned worms remaining at the end of the 14 to 24 day time period referred to above during which the worms are held at a temperature of 4 to 8° C., then these unspawned worms can be induced to spawn by adjusting the temperature of the sea water to 12 to 14° C. Generally, increasing the temperature gradually is preferred and we have found that progressively increasing the temperature at a rate of 1° C. per hour over a period of 6 to 8 hours is suitable, although the exact rate of temperature increase is not critical. The increase in temperature can conveniently be achieved by transfer of the worms to sea water (for example filtered sea water or re-circulated sea water) at a temperature of 4 to 8° C. and wherein the ambient air temperature is 12 to 14° C. For convenience the worms may be placed into portable containers of sea water at the appropriate temperature (4 to 6° C.), the container holding the sea-water and worms combination being placed in a controlled temperature room/incubator as appropriate. Under these conditions, the temperature of the sea water is gradually raised to 12 to 14° C., for example 13° C. Whilst it is preferable for the worms to be housed individually at this stage (for example in 400 ml of sea water), it is also possible for the worms to be housed in small groups of up to 20 (preferably of 10 or less, more preferably of 6 or less, for example 2, 3, 4 or 5) worms Desirably the worms will be housed in same-sex groups. The worms housed in this way are examined at approximate intervals (we have found hourly examination to be suitable).

If female worms are observed to be spawning, the eggs are obtained by placing the females in a tank containing 1 to 3 litres of sea water and allowing the worms to continue to spawn. After the majority of the eggs have been released (as may be determined by the requirement for larvae) the female can be removed and rehoused. Conveniently, a volume of sea water sufficient to provide a concentration of 100,000 eggs per litre is added prior to addition of sperm. (We generally find that a volume of 2 to 4 litres sea water is typically required, depending upon the fecundity of the female.)

If male worms are observed to be spawning, the sperm is taken into a pipette or syringe before it becomes thoroughly mixed with sea water. This reduces the spontaneous activation of the spermatozoa. A concentrated sperm mixture obtained in this way can be maintained at 5° C. for up to 48 hours without loss of viability and used as required. The sperm can by introduced into the egg/sea water mixture described above to provide a sperm concentration of $10^5$ to $10^6$ sperm per millilitre. Sperm concentration can be determined by use of a haematocytometer which is a microscope slide with etched divisions and graduations defining a known volume in the space beneath the cover slip. Typically the concentration of sperm will be calculated from the observation of the average nuclear of sperm seen in a survey of 30 defined volumes. The sperm concentration could also be estimated by a man of ordinary skill in the art, by adding approximately the sperm released by a male to 50 ml sea water then adding 1 ml of this mixture to one litre of egg/sea water mixture. In the event that the female worms are spawning, but the male worms are not, it may be desirable to induce immediate spawning of the male worms, as the unfertilised eggs of the female worms have a limited viability. Immediate spawning of the male worms treated as described above can be achieved by injection of the male worms with the fatty acid 8, 11, 14-eicosatrienoic acid, to give a final coelomic concentration of 13 µg/g body mass or an in vitro concentration of $4.5 \times 10^{-5}$ M made by dilution of a methanol solution with fine (eg. 0.2 µm) filtered sea water or sterile water or distilled water and injected to give a final methanol concentration in the body tissues of 1% v/v.

Once the sperm and the eggs have been mixed together for a period of approximately 15 minutes, the eggs may be counted (for example by randomised sub-sampling) and transferred to suitable containers (such as shallow plastic trays) at a concentration of approximately 10,000 fertilised eggs/litre. The larvae, once hatched, can then be cultured accordingly, for example as described in WO-A-03/007701.

The parent worms may be maintained at a temperature of 16 to 20° C., but provided with suitable substrate housing and organic materials as foodstuff.

Optionally the worms may be held at a reduced temperature of 6 to 8° C. for 2 to 3 days before being returned to culture conditions. Using the methodology described above it is possible to induce sexual maturation in both male and female worms of the family Arenicolidae only a few months after previous spawning of these worms. Such induction of sexual maturation of these animals has no known precedent, the animals spawning only once per annum in the wild.

Using the methodology described above it is now possible to breed lugworms throughout the whole year.

The present invention will now be further described with reference to the following non-limiting examples.

EXAMPLE 1

Induction of Sexual Maturation in the lugworm *Arenicola marina*

Male and female *Arenicola* sp. were collected from Hauxley beach, Northumberland during the summer of 2002. Male and female *Arenicola* sp. were also collected from growth trials that had been carried out at Seabait Ltd, Northumberland, United Kingdom.

Animals were introduced into concrete culture beds (broodbeds) containing decomposed organic food and sand as described in WO-A-03/007701. The animals were left for several months until required. At a specified time during November/December 2002 a group of approximately 50 of the animals were removed and a coelomic biopsy was performed and maturity status was determined. Selected animals were then transferred into a small box containing sand previously used in broodbeds for *Arenicola* sp. and the small box placed in a controlled temperature room held at 6° C. ±1° C. After 21 days at that temperature animals were removed from the substrate and placed into separate pots containing filtered sea water. Any waste material that was depurated was removed with a pipette and discarded. Once rehoused into the separate pots all animals were re-sampled and given a number/code. Animals were then gradually conditioned to 13° C. Sperm was collected from spawning males in concentrated form and stored in labelled glass vials in the refrigerator at approximately 4° C. Females that were spawning were removed from the small housing pots and placed into individual labelled aquarium tanks and the seawater made up to 2 litres using filtered seawater. Each female was allowed to continue spawning in the aquarium tank until the batch-spawning event was deemed complete. At the termination of the spawning event the female was removed from the aquarium tank and returned into the previously labelled pot provided with fresh sea water. (The weight of the animal was recorded if the animal had not commenced spawning before the point of sampling.)

The water and eggs in the tank were mixed to give a homogenous mixture, from which five to ten samples of 0.5 ml were removed and an estimate of the total number of eggs determined (Table 1). All details of provenance and usage were also recorded in this table. Sperm, from two different males (L29♂0.8 and L23♂0.1; Table 1), was added to the aquarium and the eggs left to fertilise for 10 minutes. Volumes of water from the aquarium tank containing fertilised eggs were then transferred to white, shallow trays and made up to 5 litres which resulted in a final concentration of between 7 to 10,000 eggs per litre. Trays were labelled and held at 13° C.±1° C. After 7 to 8 days the total content of the tray was poured into an aquarium tank, which resulted in a homogenous mixture of eggs and water. Six replicate one-millilitre samples were removed from the tank and larval numbers were assessed. Total larval numbers and overall survival was determined for each tray.

TABLE 1

Example of data sheet and sampling of eggs for spawning

| Female Ref. | L29♀.4 | L29♀.5 | L29♀.6 | L29♀.7 |
|---|---|---|---|---|
| Conditions/temp ° C. | Cold T/6-8 | Cold T/6-8 | Cold T/6-8 | Cold T/6-8 |
| Cold treatment period (days) | 21 | 21 | 21 | 21 |
| Initial wt (g) | 3.7 | 3.9 | | |
| Sperm added (ml) | 6 | 6 | 6 | 8 |
| Fertilisation time (mins) | 10 | 10 | 10 | 10 |
| Count/ 1 ml or 0.5 ml | 20 | 40 | 35 | 97 |
| | 44 | 46 | 31 | 112 |
| | 19 | 47 | 29 | 134 |
| | 29 | 57 | 29 | 129 |
| | 44 | 42 | 32 | 141 |
| Σ | 156 | 232 | 156 | 613 |
| Mean | 31.2 | 46.4 | 31.2 | 122.6 |
| Sd | 12.3 | 6.6 | 2.5 | 17.9 |
| Vol. Of sample (ml) | 0.5 | 0.5 | 0.5 | 0.5 |
| Total volume (ml) | 2000 | 2000 | 2000 | 2000 |
| Water used (R/F) | R | R | R | R |
| Total (N) | 124800 | 185600 | 124800 | 490400 |
| Trays | 3 | 4 | 3 | 10 |
| No./tray | 41600 | 46400 | 41600 | 49040 |

Larval counts are shown in Table 2.

TABLE 2

Results from larval counts
Larval Counts (mean of six replicate 1 ml samples)

| Female | L29♀.4 | L29♀.5 | L29♀.6 | L29♀.7 |
|---|---|---|---|---|
| Date | Jul. 1, 2003 | Jul. 1, 2003 | Jul. 1, 2003 | 7103 |
| Tray No | | | | |
| 1 | 7 | 9 | 5 | 14 |
| 2 | 2 | 14 | 9 | 15 |
| 3 | 13 | 14 | 9 | 13 |
| 4 | | 13 | | 15 |
| 5 | | | | 7 |
| 6 | | | | 6 |
| 7 | | | | 8 |
| 8 | | | | 7 |

TABLE 2-continued

Results from larval counts
Larval Counts (mean of six replicate 1 ml samples)

|   |   |   |   |   |
|---|---|---|---|---|
| 9 |   |   |   | 12 |
| Σ | 22 | 50 | 23 | 97 |
| μ | 7 | 13 | 8 | 11 |
| Total in all trays | 36667 | 62500 | 38333 | 53889 |
| Total nominal survival (%) | 88.1 | 134.7 | 92.1 | 109.9 |
| Total larvae | 110000 | 250000 | 115000 | 538889 |

EXAMPLE 2

Re-initiation of maturation in the lugworm *Arenicola marina*

A sample of worms which underwent the prescribed treatment of cold and successfully produced and spawned eggs and sperm in November and December 2002 as described in Example 1 were reconditioned into enriched broodbeds containing algae (as described in WO-A-03/007701) in December 2002 following spawning. After two months in the enriched broodbeds the animals were removed from the bed and placed into a pot of filtered sea water and held at a temperature of 6° C. for 48 hours. After this cold treatment the animals were gradually reconditioned into warm water conditions for a further 2 months. Animals were tested periodically using methods of coelomic biopsy for maturity assessment.

At a late stage of maturation the animals were removed from the broodbed and segregated into individual pots of sea water as described in Example 1. The animals were sampled and then placed into cold conditioning (6° C.) for 21 days. The following methodologies were carried out to initiate spawning and the controlled fertilisation of eggs and production of larvae. Spawning was successfully initiated in both males and females. Results from some of the females are presented in Table 3. Larval counts from the samples are presented in Table 4.

TABLE 3

Details of out-of-season spawning by
*Arenicola* sp. after re-initiation of maturation via
cold treatment and growth in enhanced substrates.

| Female Ref. | L26.♀1 | L26.♀2 | L26.♀3 | L26.♀4 |
|---|---|---|---|---|
| Temp. ° C. | 6-8 | 6-8 | 6-8 | 6-8 |
| Cold treatment period (days) | 21 | 21 | 21 | 21 |
| Sperm added (ml) | 8 | 8 | 8 | 8 |
| Fertilisation time (mins) | 10 | 10 | 10 | 10 |
| Count/ | 36 | 79 | 21 | 8 |
| 1 ml or | 25 | 67 | 19 | 12 |
| 0.5 ml | 29 | 73 | 34 | 8 |
|  | 68 | 92 | 35 | 5 |
|  | 25 | 55 | 25 | 8 |
| Σ | 183 | 366 | 134 | 41 |
| Mean | 36.6 | 73.0 | 26.8 | 8.2 |
| Sd | 18.1 | 13.8 | 7.4 | 2.5 |
| Vol. Of sample (ml) | 0.5 | 0.5 | 0.5 | 0.5 |
| Total volume (ml) | 2000 | 2000 | 2000 | 2000 |
| Water used (R/F) | R | R | R:F | R |
| Total (N) | 146400 | 292800 | 107200 | 32800 |
| Trays | 3 | 6 | 3 | 1 |
| No./tray | 48800 | 48800 | 35733 | 32800 |

R = recirculated seawater,
F = filtered seawater.

TABLE 4

Larval counts/survival of larvae 7 to 8
days after fertilisation (applicable to Table 3)
Larval Counts (mean of six replicate 1 ml samples)

| Female Date Tray No. | L26.♀1 | L26.♀2 | L26.♀3 | L26.♀4 |
|---|---|---|---|---|
| 1 | 5 | 6 | 5 | 4 |
| 2 | 7 | 6 | 2 |   |
| 3 | 4 | 4 | 3 |   |
| 4 |   | 6 |   |   |
| 5 |   | 4 |   |   |
| 6 |   | 5 |   |   |
| Σ | 16 | 31 | 10 | 4 |
| μ | 5 | 5 | 3 | 4 |
| Total in all trays | 26667 | 25833 | 16333 | 22000 |
| Total survival (%) | 55 | 53 | 46 | 67 |
| Total larvae | 80000 | 155000 | 49000 | 22000 |

Larval survival was lower than those obtained during the breeding period.

EXAMPLE 3

Using temperature manipulation to extend the period of spawning in cultured populations of *Arenicola marina* resulting in spawning up to 6 months later than the natural breeding season It is possible to extend the breeding season of *A. marina* by manipulation of the water temperature of beds used to house the animals. The final stages of maturation leading to spawning of *A. marina* can be controlled by maintaining the water temperature above 13° C. Dropping the temperature below 13° C. initiates final maturation and consequently results in spawning by both males and female *A. marina* at times substantially different to the natural breeding season. This substantially improves the efficiency of the lugworm culture system.

Some degradation of eggs within the coloemic cavity occurs when females, housed in suitable substrates, are maintained at elevated temperatures (temperatures above 13° C.) for prolonged periods of time (in excess of 2 months). There is variation in egg condition within and between females. There is nevertheless a significant production of fertilisable eggs and or sperm outside the breeding season and the embryos and larvae so produced can be reared in the standard culture conditions as previously described (see WO-A-03/007701).

The observed time of spawning for *Arenicola marina*, in the wild in Northumberland, UK was recorded between Oct. 30, 2002 and Nov. 4, 2002.

In excess of two hundred animals were each housed in Beds L29, L28, L26, L25, L24 and L23 over the summer period (May to September 2002) and maintained thereafter for various periods of time as described below. The water temperature provided in the beds was maintained above 13° C. The change in maturity status of *A. marina* in each bed was monitored via sampling of worms using method of coelomic biopsy as described previously. Animals were assessed and, when deemed suitably mature (see above) the worms were removed and exposed to a cold treatment comprising exposure to 6 to 8° C. for periods of up to 21 days.

Worms were removed from beds at the times presented in Table 5.

TABLE 5

The timing at which worms were removed
from the beds and placed into cold treatment.

| Month | Bed (worms removed for cold treatment) |
|---|---|
| November | L25, L29, L26 |
| December | L23, L24 |
| January | L28, L29 |
| February | L24 |
| March | Mature animals were available from L23 but larvae were not produced. |
| April | Mature animals were available from L23 but larvae were not produced. |
| May | L23 |

By the methods described it was possible to achieve fertilisation success in eggs derived from these worms in all months from November 2002 to May 2003 (Mature animals were present in March and April). Survival rates for larvae in May was lower than might be achieved at other times being approximately 20-30% but given the high fecundity of lugworms this nevertheless provides a means by which to obtain substantial numbers or larvae outside the natural breeding season. The standard cold treatment technologies resulted in spawning after the specified 14 to 21 days.

Tables 6a-c. provide specific examples of treatments producing spawning animals and viable larvae outside the normal breeding season.

The effectiveness of these treatments may be further improved by keeping the larvae prior to being stocked out to the production system. The larvae of *A. marina* can be held in trays with sand and static or recirculating seawater in excess of 6 months with minimum observed mortality (<20%). By combining these approaches larvae can be effectively stocked out to production beds throughout the year.

TABLE 6a

Batch 1 - Examples of females and males used for
fertilisation procedures 2002/2003

| | Batch Batch 1 | | |
|---|---|---|---|
| Date | Aug. 11, 2002 | Aug. 11, 2002 | Aug. 11, 2002 |
| Female Ref. | L26♀14 | L26♀15 | L26♀16 |
| Origin | L26 | L26 | L26 |
| Temp. ° C. | 6-8 | 6-8 | 6-8 |
| Cold treatment period (days) | 14 | 14 | 14 |
| Initial wt (g) | 6.3 | 3.4 | 4.1 |
| Sperm added (ml) | 5 | 5 | 5 |
| Males | H.♂1a ♂♂♂ mix H | H.♂B.4 H.♂B.5 | H.♂B.5 L26.♂9 |
| Fertilisation time (mins) | 10 | 10 | 10 |
| Count/ 1 ml or 0.5 ml | 11 8 18 28 8 | 23 24 24 16 10 | 38 45 49 44 37 |
| Σ | 73 | 97 | 213 |
| Mean | 14.6 | 19.4 | 42.6 |
| Sd | 8.5 | 6.2 | 5.0 |
| vol. of sample (ml) | 1.0 | 1.0 | 0.5 |
| total volume (ml) | 5000 | 5000 | 2000 |
| water used (R/F) | R | R | R |
| Total (N) | 73000 | 97000 | 170400 |
| Trays | 2 | 2 | 5 |
| No./tray | 36500 | 48500 | 34080 |

TABLE 6b

Batches 3 and 4; Examples of females and males used for fertilisation procedures 2002/2003

| | Batch | | | | | |
|---|---|---|---|---|---|---|
| | Batch 3 | | | Batch 4 | | |
| Date | Jul. 1, 2003 | Aug. 1, 2003 | Aug. 1, 2003 | Feb. 15, 2003 | Feb. 16, 2003 | Feb. 16, 2003 |
| Female Ref. | L23♀.9 | L24♀.8 | L24♀.10 | L28♀2 | L29♀10 | L28♀2 |
| Origin | L23 | L24 | L24 | | | |
| Temp. ° C. | 6-8 | 6-8 | 6-8 | 6-8 | 6-8 | 6-8 |
| Cold treatment period (days) | 21 | 21 | 21 | 21 | 21 | 21 |
| Initial wt (g) | 5.3 | 12.1 | 8.5 | unk | unk | unk |
| Sperm added (ml) | 6 | 5 | 5 | 6 | 4 | 3 |
| Males | L23♂.3 L24♂.1, 7 | L24♂.5 | L24♂.5 | L28♂.9 L28♂.3 | L28♂.9 L28♂.11 | L28♂.9 L28♂.11 |
| Fertilisation time (mins) | 10 | 10 | 10 | 15 | 15 | 15 |
| Count/ 1 ml or 0.5 ml | 44 52 43 52 50 | 17 17 10 23 13 | 42 71 56 41 54 | 30 41 39 30 31 | 70 56 39 44 39 | 5 7 10 8 14 |
| Σ | 241 | 80 | 264 | 171 | 248 | 44 |
| Mean | 48.2 | 16 | 52.8 | 34.2 | 49.6 | 8.8 |
| Sd | 4.4 | 4.9 | 12.2 | 5.4 | 13.4 | 3.4 |
| vol. of sample (ml) | 0.5 | 0.5 | 0.5 | 0.5 | 0.5 | 0.5 |
| total volume (ml) | 2000 | 2000 | 2000 | 4300 | 2000 | 2000 |
| water used (R/F) | R | R | R | F | F | F |
| Total (N) | 192800 | 64000 | 211200 | 294120 | 198400 | 35200 |
| Trays | 2 | 1 | 3 | 6 | 4 | 1 |
| No./tray | 96400 | 64000 | 70400 | 49020 | 49600 | 35200 |

TABLE 6c

Batch 6; Examples of females and males used for fertilisation procedures 2002/2003

| | Batch Batch 6 | | |
|---|---|---|---|
| Date | May 13, 2003 | May 13, 2003 | May 13, 2003 |
| Female Ref. | L23♀1 | L23♀2 | L23♀9 |
| Origin | L23 | L23 | L23 |
| Temp. °C. | 6-8 | 6-8 | 6-8 |
| Cold treatment period (days) | 21 | 21 | 21 |
| Initial wt (g) | unk | unk | unk |
| Sperm added (ml) | 7 | 7 | 7 |
| Males | L23♂.3 Ctroom; 6° C. | L23♂.3 | L23♂.3 |
| Fertilisation time (mins) | 20 | 20 | 20 |
| Count/ | 192 | 122 | 165 |
| 1 ml or | 109 | 101 | 112 |
| 0.5 ml | 117 | 111 | 152 |
| | 139 | 105 | 133 |
| | 171 | 85 | 141 |
| Σ | 728 | 524 | 703 |
| Mean | 145.6 | 104.8 | 140.6 |
| Sd | 35.4 | 13.6 | 20.0 |
| vol. of sample (ml) | 0.5 | 0.5 | 0.5 |
| total volume (ml) | 2000 | 3000 | 2000 |
| water used (R/F) | R | R | R |
| Total (N) | 582400 | 628800 | 562400 |
| Trays | 1 | 4 | 1 |
| No./tray | 150000 | 157200 | 150000 |

Key:
L—bed code;
unk—unknown;
R—recirculated, filtered sea water;
F—filtered sea water

REFERENCES

Babcock et al., (1986) Marine Biology, 90, 379-394.

Bentley, M. G., Clark, S., Pacey, A. A. (1990). "The role of arachodonic acid and eicostarienoic acids in the activation of spermatozoa in *Arenicola marina* L. Annelida :Polychaeta ". Biological Bulletin 178 (1): 1-9.

Bentley, M. G. and Hardege, J. D. (1996). "The role of the fatty acid hormone in the reproduction of the polychaete *Arenicola marina*". Invertebrate Reproduction and Development 30 (1-3): 159-165.

Clark, R. B., and Olive, P. J. W. (1973). "Recent advances in polychaete endocrinology and reproductive biology." *Oceanography and marine biology, annual review*, 11, 176-223.

D'Asaro et al., 1976, in "Lugworm Aquaculture", Report No. 16, State University System of Florida, Sea Grant College Program (FLA Reg. 3:331/16/976).

Fauchald, K., and Jumars, P. A. (1979). "The diet of worms: a study of polychaete feeding guilds." *Oceanography and Marine Biology: Annual Review*, 17, 193-284.

Gambi, M. C., Castelli, A., Giangrande, A., Lanera, P., Prevedelli, D., and Zunarelli-Vandini, R. (1994). "Polychaetes of commercial and applied interest in Italy: an overview." *Memoires de la Musee nationale d' Histoire naturelle*, 162, 593-603.

Jumars, P. A. (1993). "Gourmands of mud: diet selection in marine deposit feeders." Diet Selection: An inter-disciplinary Approach to Foraging Behaviour, R. N. Hughes, ed., Blackwell Scientific, Oxford, 124-156.

Olive, P. J. W. (1993). "Management of the exploitation of the Lugworm *Arenicola marina* and the Ragworm *Nereis virens* (Polychaeta) in conservation areas." *Aquatic Conservation: Marine and Freshwater Ecosystems*, 3(1), 1-24.

Watson et al., (2000) Marine Biology, 163, 1003-1017.

The invention claimed is:

1. A method of inducing gamete maturation to be competent to fertilise in marine worms of the family Arenicolidae which exhibit epidemic spawning, said method comprising:
    providing maturing male and/or female worms in a housing substrate in sea water at a temperature of 4 to 8° C. for a time period of 14 to 24 days.

2. The method as claimed in claim 1 wherein the worms are maintained at a temperature of 5 to 7° C. for 20 to 22 days.

3. A method for inducing spawning of marine worms of the family Arenicolidae which exhibit epidemic spawning, said method comprising inducing gamete maturation by the method of claim 1, and further comprising exposing the worms to a hormone able to induce gamete release.

4. The method of claim 3 wherein said worms are male worms and said hormone is 8, 11, 14-eicosatrienoic acid.

5. The method of claim 3 wherein said worms are female worms and said hormone is provided as an homogenate of prostomium.

6. A method for inducing spawning of marine worms of the family Arenicolidae and which exhibit epidemic spawning, said method comprising inducing gamete maturation by the method of claim 1, and further including raising the temperature of the sea water to 12 to 14° C.

7. The method as claimed in claim 6 wherein the temperature of the sea water is increased at a rate of 1° C. per hour to 12 to 140° C.

8. The method as claimed in claim 1 wherein said marine worms are *Arenicolidae marina* or *Arenicola defadiens*.

9. The method as claimed in any claim 1 wherein said substrate is sand.

10. The method as claimed in claim 1 wherein said marine worms are cultured worms which have previously been maintained at a temperature of 14 to 16° C. for at least one month.

* * * * *

UNITED STATES PATENT AND TRADEMARK OFFICE
CERTIFICATE OF CORRECTION

PATENT NO. : 7,568,446 B2  Page 1 of 1
APPLICATION NO. : 10/577790
DATED : August 4, 2009
INVENTOR(S) : Peter James William Olive It is certified that error appears in the above-identified patent and that said Letters Patent is hereby corrected as shown below:

Column 12, Line 43, Claim 7 – change "140°C" to --14°C--

Column 12, Line 45, Claim 8 – change "defadiens" to --defodiens--

Signed and Sealed this

Twenty-sixth Day of January, 2010

David J. Kappos
*Director of the United States Patent and Trademark Office*